United States Patent
Bonn et al.

(10) Patent No.: US 8,965,536 B2
(45) Date of Patent: Feb. 24, 2015

(54) INTRACOOLED PERCUTANEOUS MICROWAVE ABLATION PROBE

(75) Inventors: Kenlyn S. Bonn, Boulder, CO (US);
Steven E. Butcher, Berthoud, CO (US)

(73) Assignee: Covidien LP, Mansfield, MA (US)

( * ) Notice: Subject to any disclaimer, the term of this patent is extended or adjusted under 35 U.S.C. 154(b) by 1388 days.

(21) Appl. No.: 12/395,034

(22) Filed: Feb. 27, 2009

(65) Prior Publication Data

US 2009/0222002 A1 Sep. 3, 2009

Related U.S. Application Data

(60) Provisional application No. 61/033,196, filed on Mar. 3, 2008.

(51) Int. Cl.
*A61N 1/00* (2006.01)
*A61B 18/18* (2006.01)
*A61B 17/00* (2006.01)
*A61B 18/00* (2006.01)

(52) U.S. Cl.
CPC .............. *A61B 18/18* (2013.01); *A61B 18/1815* (2013.01); *A61B 2017/00084* (2013.01); *A61B 2018/00023* (2013.01)
USPC .......................................... 607/156; 604/154

(58) Field of Classification Search
CPC ........... A61B 2018/00791; A61B 2018/00577; A61B 2017/00084; A61B 2018/00005; A61B 18/18; A61B 18/1815; A61B 2018/00023
USPC ............... 606/32–50; 607/154, 156, 101–105
See application file for complete search history.

(56) References Cited

U.S. PATENT DOCUMENTS

| | | |
|---|---|---|
| 5,275,597 A | 1/1994 | Higgins et al. |
| 5,348,554 A | 9/1994 | Imran et al. |
| 5,556,377 A | 9/1996 | Rosen et al. |
| 5,810,804 A | 9/1998 | Gough et al. |
| 6,059,780 A | 5/2000 | Gough et al. |
| 6,506,189 B1 | 1/2003 | Rittman, III et al. |
| 6,575,969 B1 | 6/2003 | Rittman, III et al. |
| 6,599,288 B2 | 7/2003 | Maguire et al. |
| 6,613,047 B2 | 9/2003 | Edwards |
| 6,974,463 B2 | 12/2005 | Magers et al. |
| 7,311,703 B2 | 12/2007 | Turovskiy et al. |
| 2003/0065317 A1 | 4/2003 | Rudie et al. |

(Continued)

FOREIGN PATENT DOCUMENTS

| | | |
|---|---|---|
| EP | 0608609 | 8/1994 |
| WO | 9634571 | 11/1996 |

(Continued)

OTHER PUBLICATIONS

European Search Report for European Application No. 11164913.3 dated Feb. 22, 2012.

(Continued)

*Primary Examiner* — Nicholas Lucchesi
*Assistant Examiner* — Weng Lee

(57) ABSTRACT

The present disclosure relates to devices and methods for the treatment of tissue with microwave energy. The devices and methods disclosed herein incorporate an antenna assembly comprising outer and inner conductors having a dielectric material interposed therebetween, a sealing barrier, and a cooling system to minimize the likelihood that the antenna assembly will overheat.

16 Claims, 16 Drawing Sheets

(56) References Cited

U.S. PATENT DOCUMENTS

| | | |
|---|---|---|
| 2005/0015081 A1* | 1/2005 | Turovskiy et al. .............. 606/33 |
| 2005/0149010 A1 | 7/2005 | Turovskiy et al. |
| 2005/0182393 A1 | 8/2005 | Abboud et al. |
| 2005/0245920 A1 | 11/2005 | Vitullo et al. |
| 2006/0241576 A1 | 10/2006 | Diederich et al. |
| 2006/0276780 A1 | 12/2006 | Brace et al. |
| 2007/0078454 A1 | 4/2007 | McPherson |
| 2007/0203551 A1 | 8/2007 | Cronin et al. |
| 2008/0021448 A1 | 1/2008 | Orszulak et al. |
| 2008/0135217 A1 | 6/2008 | Turovskiy |
| 2008/0183165 A1 | 7/2008 | Buysse et al. |

FOREIGN PATENT DOCUMENTS

| | | |
|---|---|---|
| WO | 9706739 | 2/1997 |
| WO | 9706740 | 2/1997 |
| WO | 9706855 | 2/1997 |
| WO | 0012010 | 3/2000 |
| WO | 0100114 | 1/2001 |
| WO | 2005011049 | 2/2005 |
| WO | 2007076924 | 7/2007 |
| WO | 2007112081 | 10/2007 |
| WO | WO 2008008545 | 1/2008 |

OTHER PUBLICATIONS

Partial European Search Report, Application No. 09003029, dated May 20, 2009.

European Search Report, Application No. EP 09 00 3029 dated May 20, 2009.

\* cited by examiner

INTRACOOLED PERCUTANEOUS MICROWAVE ABLATION PROBE

CROSS-REFERENCE TO RELATED APPLICATIONS

This application claims the benefit of priority to U.S. Provisional Application Ser. No. 61/033,196 entitled "INTRACOOLED PERCUTANEOUS MICROWAVE ABLATION PROBE" filed Mar. 3, 2008 by Kenlyn Bonn et al, which is incorporated by reference herein.

BACKGROUND

1. Technical Field

The present disclosure relates generally to microwave antennas for use in therapeutic or ablative tissue treatment applications. More particularly, the present disclosure relates to devices and methods for regulating, maintaining, and/or controlling the temperature of microwave antennas used in such treatment applications.

2. Background of the Related Art

Many procedures and devices employing microwave technology are well known for their applicability in the treatment, coagulation, and targeted ablation of tissue. During such procedures, a microwave probe antenna of the monopole, dipole, or helical variety, as is conventional in the art, is typically advanced into the patient, either laparoscopically or percutaneously, to reach target tissue.

Following introduction of the microwave probe, microwave energy is transmitted to the target tissue, which may cause the outer surface of the antenna to sometimes reach unnecessarily high temperatures via ohmic heating. Additionally, or alternatively, losses in the feedline, through which energy is communicated to the antenna from a power source, may contribute to heating in the antenna. When exposed to such temperatures, the treatment site, as well as the surrounding tissue, may be undesirably effected.

To prevent unnecessarily high temperatures, and the corresponding undesirable effects upon the tissue, several different cooling methodologies are conventionally employed. For example, microwave probes may include external cooling jackets. However, employing these jackets increases the overall size, i.e., the gauge size of the instrument, and consequently, the invasiveness of the procedure. As such, there exists a continuing need in the art for an improved microwave tissue treatment device that includes a cooling system to avoid the realization of unnecessarily high temperatures during treatment, as well as the gauge size of the device, and thereby minimize undesirable effects on the tissue.

SUMMARY

In one aspect of the present disclosure, a microwave tissue treatment device for the therapeutic treatment or ablation of tissue is disclosed. The microwave tissue treatment device includes an antenna assembly having proximal and distal ends. The antenna assembly includes an elongate member, an outer conductor positioned within the elongate member, a dielectric material disposed within the outer conductor and defining a lumen and one or more longitudinally extending channels, an inner conductor including a distal radiating section and being at least partially disposed within the lumen, a sealing barrier disposed adjacent a distal end of the outer conductor, a radiating portion, and a cooling system.

The radiating portion is disposed adjacent the sealing barrier, and includes the radiating section of the inner conductor as well as a sheath with proximal and distal ends that is at least partially disposed about the radiating section to define at least one cavity. The at least one cavity may include two or more regions, e.g., proximal, intermediate, and distal regions. In one embodiment, the regions of the cavity may be at least partially defined by one or more baffle members that are disposed within the cavity. Additionally, the baffle member(s) will also define, at least partially, two or more axial dimensions within the cavity.

The cooling system includes inlet and outlet conduits that are configured and dimensioned to circulate a fluid through the antenna assembly. In one embodiment of the present disclosure, the fluid may be a heat dissipative fluid that is selected from the group consisting of water, saline, ammonium chloride, sodium nitrate, and potassium chloride. The inlet and outlet conduits are at least partially disposed within the channel or channels of the dielectric material, and are in communication with the at least one cavity such that at least a portion of the radiating section is in contact with the fluid.

It is envisioned that the channel(s) extending through the dielectric material may include at least a first channel and a second channel. In one embodiment, the inlet member(s) may be at least partially disposed in the first channel, and the outlet member(s) may be at least partially disposed in the second channel.

It is further envisioned that the microwave tissue treatment device may also include a penetrating member that is disposed at the distal end of the antenna assembly. The antenna assembly may further include a connecting hub that is positioned proximally of the sealing barrier and at least partially about the elongate member. The connecting hub includes at least one conduit that is configured and dimensioned to receive the inlet and outlet member(s) of the cooling system.

In one embodiment of the antenna assembly, the outer conductor may include one or more apertures that are configured and dimensioned to receive the inlet and outlet member(s) of the cooling system. Additionally, or alternatively, the microwave tissue treatment may also include at least one temperature sensor that is operatively connected to the radiating section.

In another aspect of the present disclosure, an improved microwave tissue treatment device is disclosed. The improved microwave tissue treatment device includes an outer conductor, an inner conductor with a radiating section, and a radiating portion that includes the radiating section of the inner conductor and a sheath that is at least partially disposed thereabout to define at least one cavity. The device also includes a cooling system with inlet and outlet conduits that are in fluid communication with the radiating section, and a dielectric material that is disposed within the outer conductor. The dielectric material includes a lumen and one or more channels that extend therethrough. The lumen extending through the dielectric material is configured and dimensioned to at least partially receive at least a portion of the inner conductor, and the channel(s) extending through the dielectric material are configured and dimensioned to at least partially receive the inlet and outlet conduits.

In one embodiment, the cooling system includes first and second channels that extend longitudinally through the dielectric material. The first and second channels at least partially accommodate the inlet and outlet conduits, respectively.

In another embodiment, the at least one cavity defined by the sheath may include at least two regions. In this embodiment, the improved microwave tissue treatment may further including one or more baffle members that are disposed within the at least one cavity to thereby divide the cavity into at least two regions.

In yet another aspect of the present disclosure, a method of cooling a microwave antenna including an inner conductor, an outer conductor, and a dielectric material is disclosed. The disclosed method includes the steps of (i) providing a cooling system with one or more inlet and outlet conduits disposed within the dielectric material and in fluid communication with the microwave antenna; and (ii) circulating a cooling fluid through the cooling system such that the cooling fluid is in fluid communication with at least a portion of the inner conductor.

In alternative embodiments, the disclosed method may further comprise the step of monitoring the temperature of the inner conductor with at least one temperature sensor operatively connected thereto, and/or regulating the circulation of the cooling fluid with a pump that is in communication with the cooling system.

These and other features of the presently disclosed microwave tissue treatment device, and corresponding method of use, will become more readily apparent to those skilled in the art from the following detailed description of various embodiments of the present disclosure.

BRIEF DESCRIPTION OF THE DRAWINGS

Various embodiments of the present disclosure are described hereinbelow with references to the drawings, wherein.

DETAILED DESCRIPTION OF THE EMBODIMENTS

Figure 1:
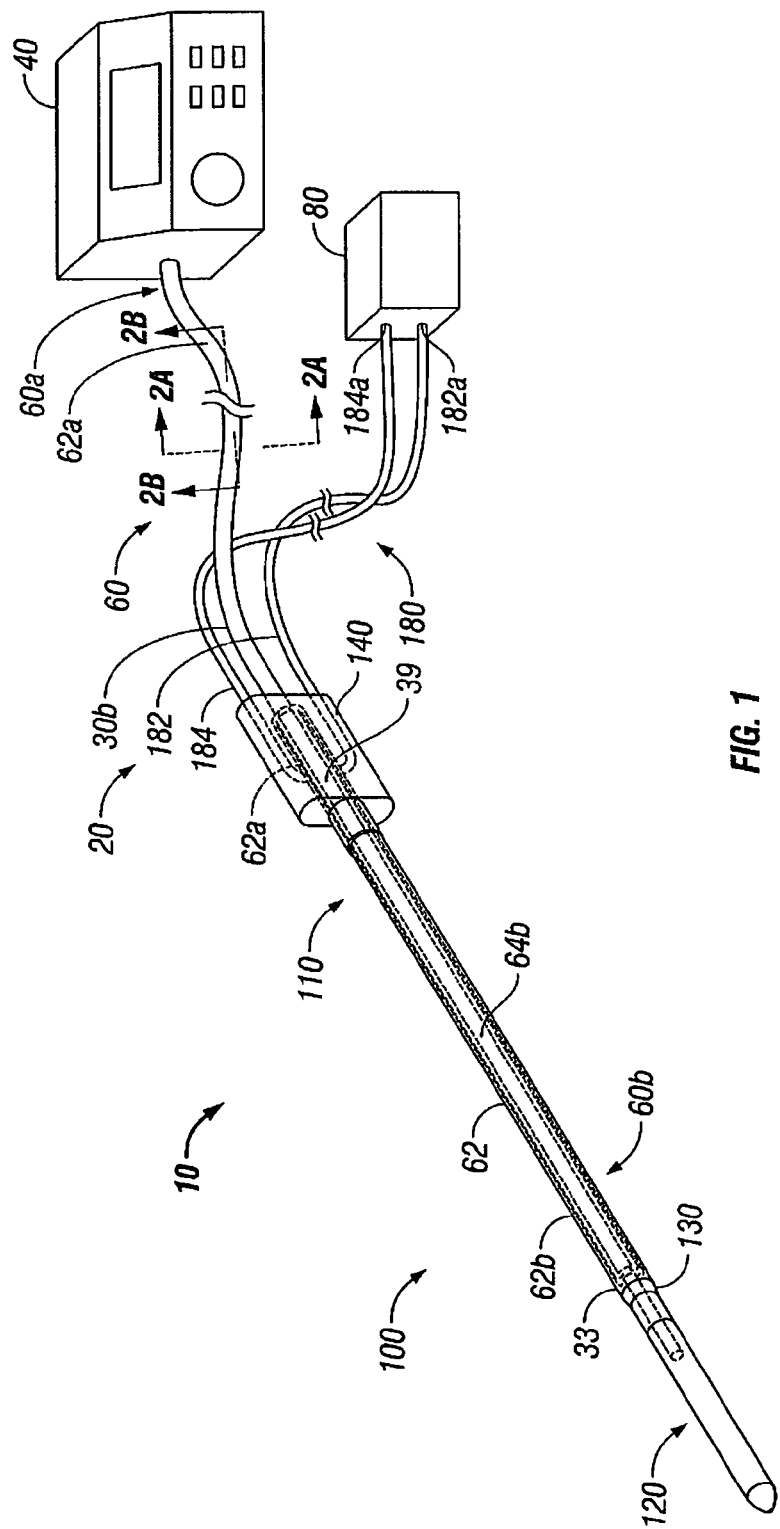
FIG. 1 is a schematic illustration of a microwave tissue treatment system including a microwave tissue treatment device, in accordance with an embodiment of the present disclosure.

Specific embodiments of the presently disclosed microwave tissue treatment device, and corresponding method of use thereof, will now be described in detail with reference to the foregoing figures wherein like reference characters identify similar or identical elements. In the drawings and in the description which follows, the term "proximal" will refer to the end of the microwave tissue treatment device, or component thereof, that is closest to the clinician during proper use, while the term "distal" will refer to the end that is furthest from the clinician, as is conventional in the art.

Referring now to FIGS. 1-4B, a microwave tissue treatment system 10 is disclosed. System 10 includes a microwave tissue treatment device 20 having an antenna assembly 100 connected to a power supply 40 through a feedline 60. Power supply 40 may be any power generating device suitable for the intended purpose of energizing tissue treatment device 20, e.g., a microwave or RF generator. Microwave tissue treatment device 20 may include one or more pumps 80, e.g., a peristaltic pump or the like, as a mechanism for circulating a cooling or heat dissipative fluid through antenna assembly 100, as described below.

Feedline 60 may range in length from about 7 feet to about 10 feet, but may be either substantially longer or shorter if required in a particular application. Feedline 60 may be composed of any suitable conductive lead capable of transferring an electrical current to tissue treatment device 20. In the embodiment seen in FIG. 2A, feedline 60 includes an elongate member 62 disposed about a coaxial cable having an inner conductor 64, an outer conductor 66, and a dielectric 68 interposed therebetween. The dielectric 68 includes respective proximal and distal portions 60a, 60b, and electrically separates and/or isolates the inner conductor 64 from the outer conductor 66. Elongate member 62 includes respective proximal and distal ends 62a, 62b, and may be any sleeve, tube, jacket, or the like formed of any conductive or non-conductive material.

Proximal portion 60a of feedline 60 is disposed proximally of antenna assembly 100 and is operatively connected to, or connectable to, power supply 40. As seen in FIG. 2B, proximal portion 60a includes and defines proximal portions 64a, 66a, and 68a of inner conductor 64, outer conductor 66, and dielectric 68, respectively. Distal portion 60b (FIG. 1) of feedline 60 forms a component of antenna assembly 100, and includes and defines respective distal portions 64b, 66b, 68b of inner conductor 64, outer conductor 66, and dielectric 68. Alternatively, however, it is envisioned that the feedline 60 may be separable from, and connectable to, the antenna assembly 100. Reference may be made to commonly owned U.S. Pat. No. 7,311,703 to Turovskiy, et al., filed Jan. 20, 2005, for further discussion of the structure of feedline 60.

The respective inner and outer conductors 64, 66 are each formed, at least in part, of a conductive material or metal, such as stainless steel, copper, or gold. In certain embodiments, the respective inner and outer conductors 64, 66 of feedline 60 may include a conductive or non-conductive substrate that is plated or coated with a suitable conductive material. In contrast, dielectric 68 is formed of a material having a dielectric value and tangential loss constant of sufficient value to electrically separate and/or isolate the respective inner and outer conductors 64, 66 from one another, including but not being limited to, expanded foam polytetrafluoroethylene (PTFE), polymide, silicon dioxide, or fluoropolymer. However, it is envisioned that dielectric 68 may be formed of any non-conductive material capable of maintaining the desired impedance value and electrical configuration between the respective inner and outer conductors 64, 66. In addition, it is envisioned that dielectric 68 may be formed from a combination of dielectric materials.

Antenna assembly 100 (FIG. 1) of microwave tissue treatment device 10 will now be discussed. Antenna assembly 100 includes a proximal portion 110, a distal or radiating portion 120, a sealing barrier 140 disposed therebetween, and a cooling system 180.

Figure 4A:
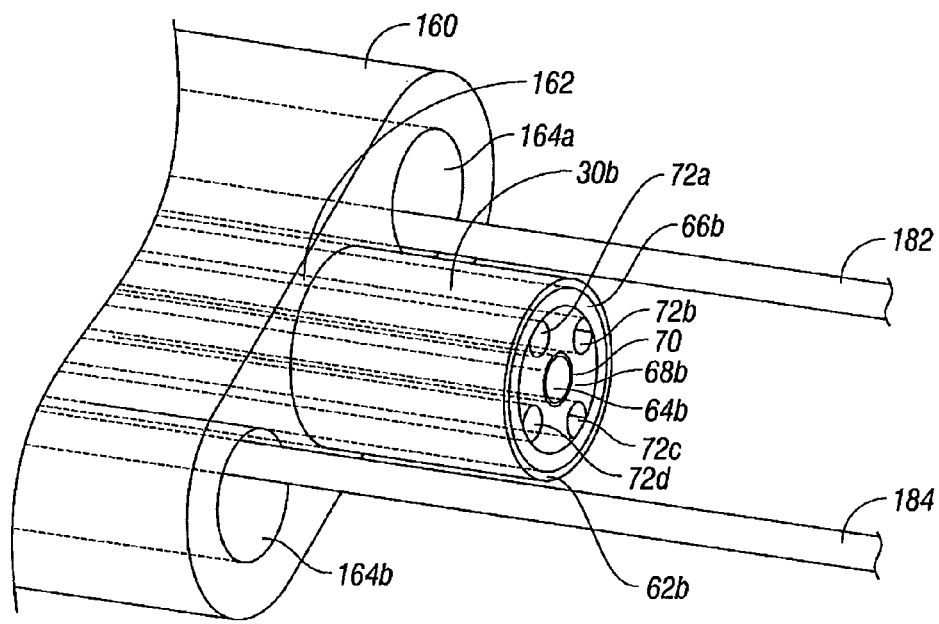
FIG. 4A is a schematic, perspective view of a connecting hub for use with the antenna assembly of the microwave tissue treatment device of FIG. 1.
Figure 4B:
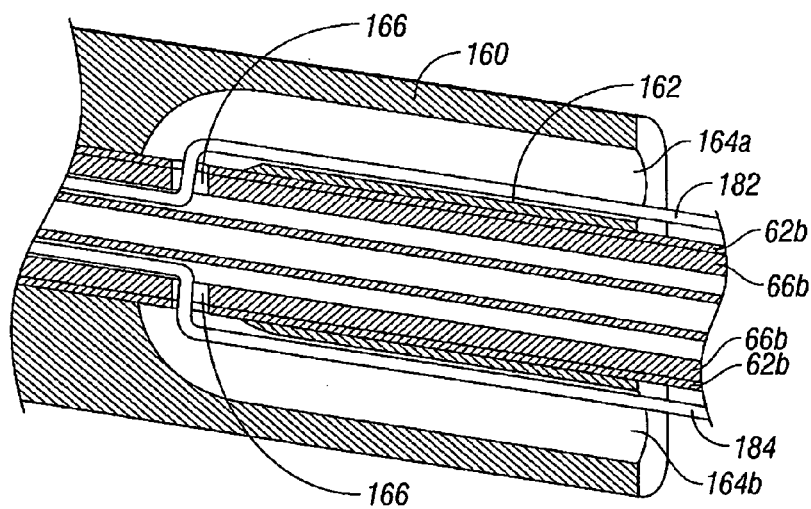
FIG. 4B is a longitudinal, cross-sectional view of the connecting hub, as taken through 4B-4B of FIG. 3.

Proximal portion 110 of antenna assembly 100 includes a connecting hub 160 and distal portion 60b of feedline 60. As seen in FIGS. 4A-4B, connecting hub 160 defines a first conduit 162 configured and dimensioned to receive distal portion 60b (FIG. 1) of feedline 60, additional conduits 164a, 164b configured and dimensioned to receive respective inlet and outlet conduits 182, 184 of cooling system 180, which is discussed in detail below, and one or more apertures 166 formed in an internal surface thereof that are configured and dimensioned to receive inlet and outlet conduits 182, 184, respectively. Connecting hub 160 may be formed of any suitable material including, but not limited to, polymeric materials.

Distal portion 68b of dielectric 68 defines a lumen 70 and a series of channels 72a-72d disposed thereabout, each extending through dielectric 68. Lumen 70 is configured and dimensioned to receive distal portion 64b of the inner conductor 64, and channels 72a-72d are configured and dimensioned to receive the respective inlet and outlet conduits 182, 184 of cooling system 180. Lumen 70 and channels 72a-72d may be formed in dielectric 68 through any suitable manufacturing method including, but not limited to extrusion, injection molding, or drilling.

Figure 5A:
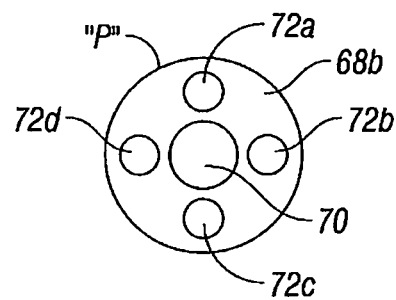
FIGS. 5A-5C are transverse, cross-sectional views of various embodiments of a dielectric for use in the microwave tissue treatment device of FIG. 1.
Figure 5B:
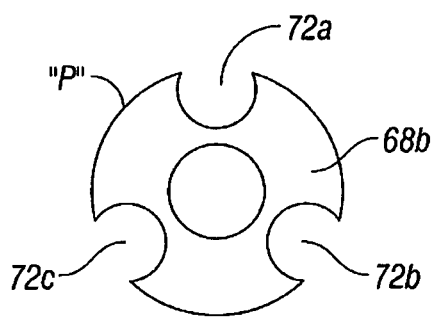
Figure 5C:
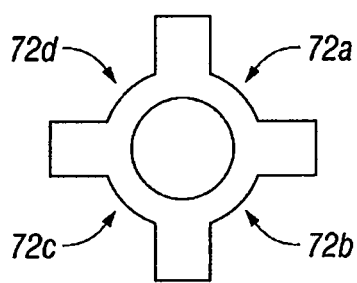

Although the embodiment of the microwave tissue treatment device 10 discussed with respect to FIGS. 1-5B is illustrated as including a distal portion 68b of dielectric 68 with a single lumen 70 and four channels, i.e., channels 72a, 72b, 72c, and 72d, that are substantially circular in cross-sectional configuration, it should be appreciated that the number and/or configuration of the lumen 70 and the channels extending through dielectric 68 may be varied depending on the air/polymer/cooling fluid ratio to match the desired impedance, e.g., 50 ohms. For example, lumen 70 and channels 72a-72d may be present in any number suitable for the intended purpose of accommodating the respective inlet and outlet conduits 182, 184 of cooling system 180, and may exhibit any suitable geometrical configuration, such as that seen in the embodiment illustrated in FIG. 5C. With reference to FIGS. 5A and 5B in particular, it is envisioned that channels 72a-72d may be oriented such that they are completely or partially defined within the perimeter "P" of distal portion 68b of dielectric 68.

Figure 2A:
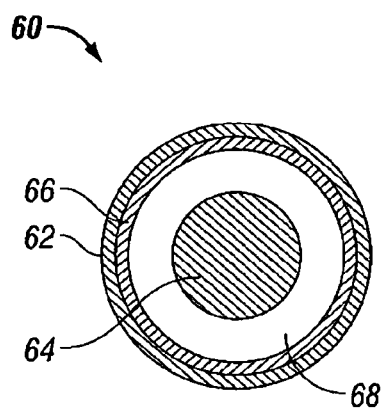
FIG. 2A is a transverse, cross-sectional view of a feedline of the microwave tissue treatment device of FIG. 1, as taken through 2A-2A of FIG. 1.
Figure 2B:
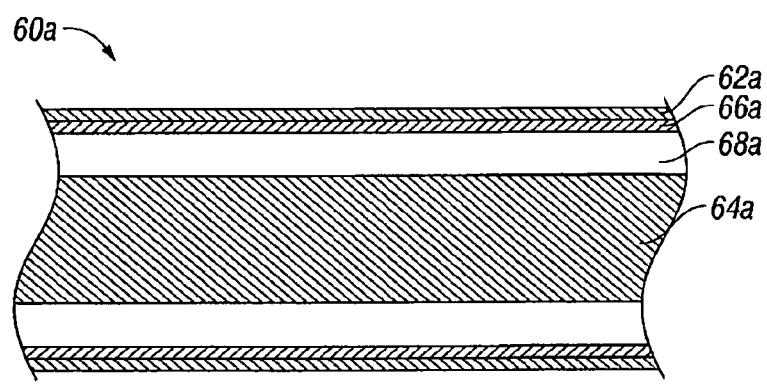
FIG. 2B is a longitudinal, cross-sectional view of a proximal portion of the feedline of the microwave tissue treatment device of FIG. 1, as taken through 2B-2B of FIG. 1.
Figure 3:
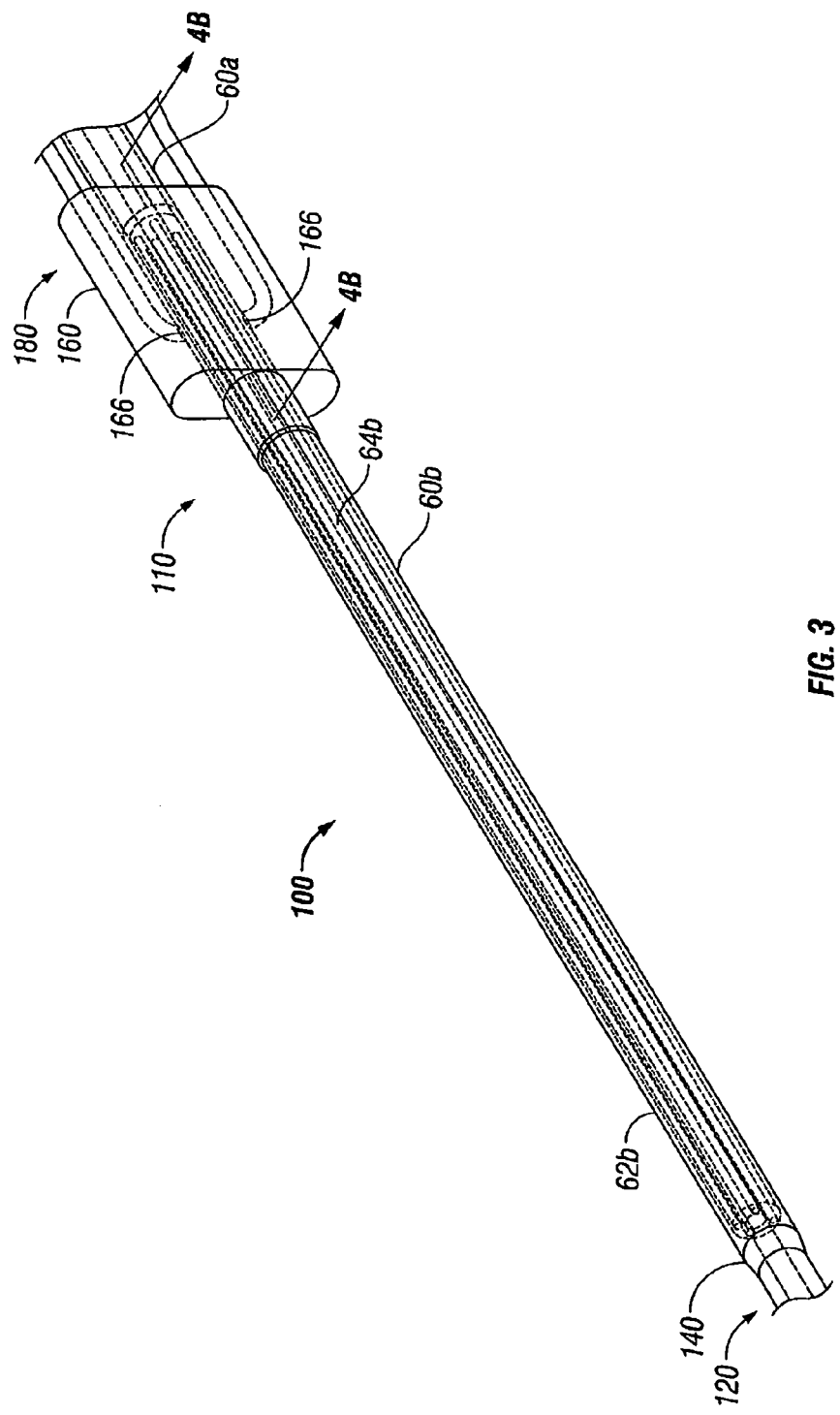
FIG. 3 is a schematic, perspective view of a proximal portion of an antenna assembly of the microwave tissue treatment device of FIG. 1.
Figure 6:
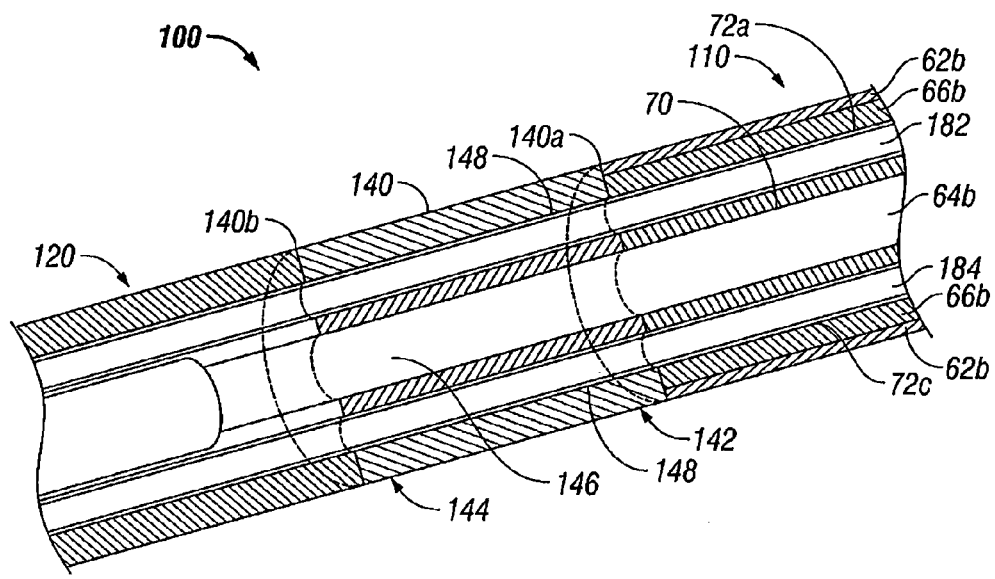
FIG. 6 is a schematic, cross-sectional, perspective view of a sealing barrier for use in the microwave tissue treatment device of FIG. 1, as taken through 6-6 of FIG. 1.

Referring now to FIGS. 1, 3, and 6, sealing barrier 140 will be discussed. Sealing barrier 140 is disposed between the respective proximal and radiating portions 110, 120 (FIG. 3) of antenna assembly 100. Sealing barrier 140 has proximal and distal ends 142, 144 (FIG. 6), respectively, and may be connected to proximal portion 110 of antenna assembly 100 in any suitable manner including, but not limited to, a snap-fit arrangement, adhesives, or a screw-type fit. Sealing barrier 140 defines a lumen 146 and one or more channels 148 that extend axially therethrough. Lumen 146 is adapted to at least partially receive distal portion 64b of inner conductor 64, and channels 148 are adapted to at least partially receive the respective inlet and outlet conduits 182, 184 of cooling system 180. Lumen 146 and channels 148 are respectively aligned with lumen 70 and channels 72a-72d (only channels 72a and 72c being shown) formed in distal portion 68b of dielectric 68 such that distal portion 64b of inner conductor 64 and the respective inlet and outlet conduits 182, 184 of cooling system 180 may extend into radiating portion 120 of antenna assembly 100.

Sealing barrier 140 may be formed of any biocompatible material suitable for the intended purpose of preventing the escape of fluids into the proximal portion 110 of antenna assembly 100, as described below. Sealing barrier 140 may be formed either of a conductive or non-conductive material, and may be either substantially rigid or substantially non-rigid in character. Sealing barrier 140 inhibits fluid from contacting both the inner conductor 64b and the outer conductor 66b, thus substantially reducing the likelihood of an electrical short. Additionally, sealing barrier 140 serves as a dielectric break allowing for the dipole construction of the microwave tissue treatment device 10 (FIG. 1).

Figure 7A:
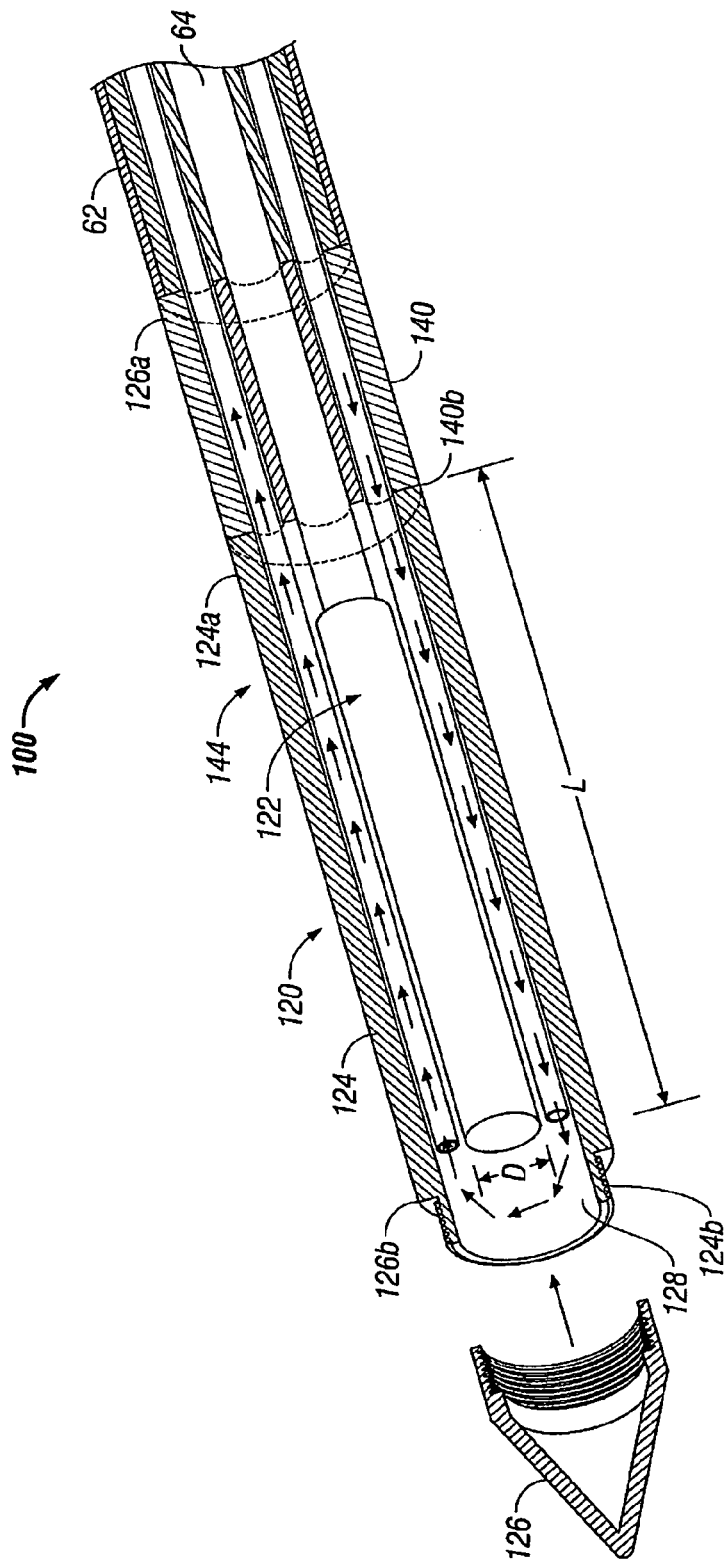
FIGS. 7A-7F are schematic, cross-sectional, perspective views of various embodiments of a radiating portion of the microwave tissue treatment of FIG. 1, as taken through 6-6 of FIG. 1.

Referring now to FIG. 7A, as discussed above, radiating portion 120 of antenna assembly 100 is disposed adjacent distal end 144 of sealing barrier 140. Radiating portion 120 includes a radiating section 122 of inner conductor 64, a sheath 124 that is at least partially disposed thereabout, and a penetrating member 126 supported on a distal end 124b of sheath 124.

Radiating section 122 of inner conductor 64 serves to transmit the microwave energy supplied by power supply 40 (FIG. 1) to a target area or target tissue (not shown). Radiating section 122 defines an axial dimension "L" and a radial dimension "D". As would be appreciated by one of ordinary skill in the art, by varying the axial and radial dimensions of the radiating section 122, the amount of microwave energy that can be transmitted to the target tissue therethrough can be regulated or controlled.

Figure 7B:
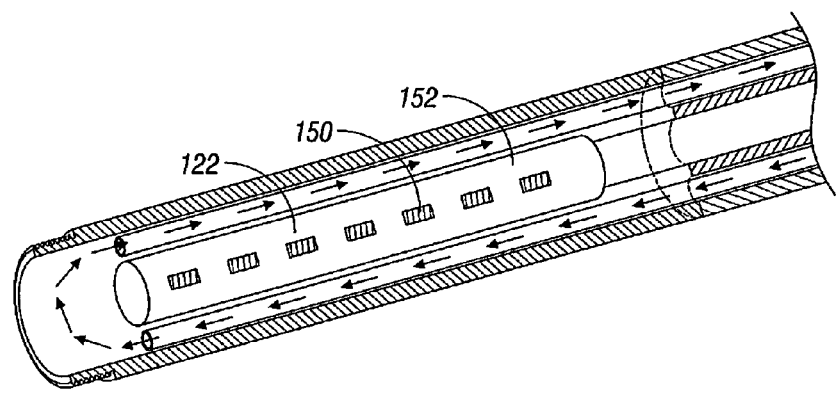

In one embodiment, as seen in FIG. 7A, radiating section 122 of inner conductor 64 may be entirely formed of a conductive material. In an alternative embodiment, as seen in FIG. 7B, radiating section 122 may only be partially formed of a conductive material. In this embodiment, radiating section 122 includes one or more conductive surfaces 150 disposed on a non-conductive substrate 152. Conductive surface, or surfaces, 150 may have a particular pattern or distribution for focusing or dispersing the energy transmitted into the radiating section 122. For example, conductive surfaces 150 may only be present on one side, or in one particular area or region of radiating section 122. Conductive surfaces 150 may be integrally formed with substrate 152, or may be fixedly or removably attached thereto.

Referring back to FIG. 7A, sheath 124 has respective proximal and distal ends 124a, 124b, and is disposed at least partially about radiating section 122 in such a manner so as to define a cavity 128. At its proximal end 124a, sheath 124 may be fixedly, releasably, and/or slidably connected to sealing barrier 140, elongate member 62, or any other suitable surface of antenna assembly 100 in any appropriate manner including, but not being limited to, the use of welds or adhesives, as would be appreciated by one skilled in the art. In the embodiment seen in FIG. 7A, distal end 124b of sheath 124 is open and configured for coupling to penetrating member 126 such that cavity 128 is defined by the penetrating member 126, sheath 124, and sealing barrier 140. In this embodiment, sheath 124 may be connected to penetrating member 126 in any suitable manner including, but not limited to, a screw-type fit, as seen in FIG. 7A, via a snap-fit arrangement, or through the use of adhesives.

Figure 7C:
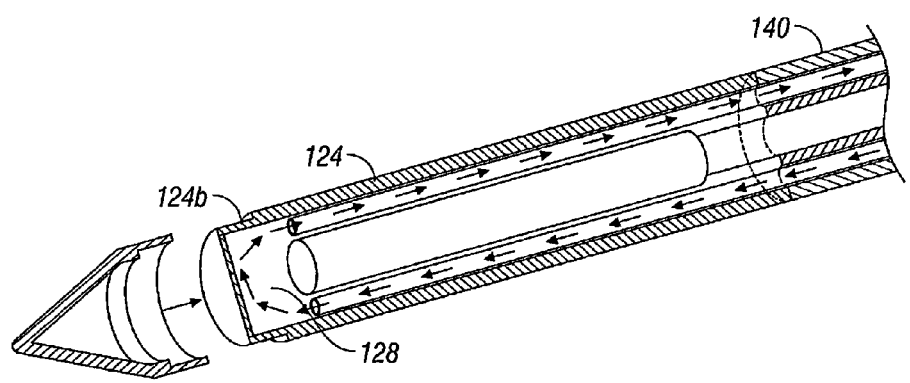

In another embodiment, as seen in FIG. 7C, distal end 124b of sheath 124 is closed or sealed such that cavity 128 is defined by sheath 124 and sealing barrier 140 only.

Figure 7D:
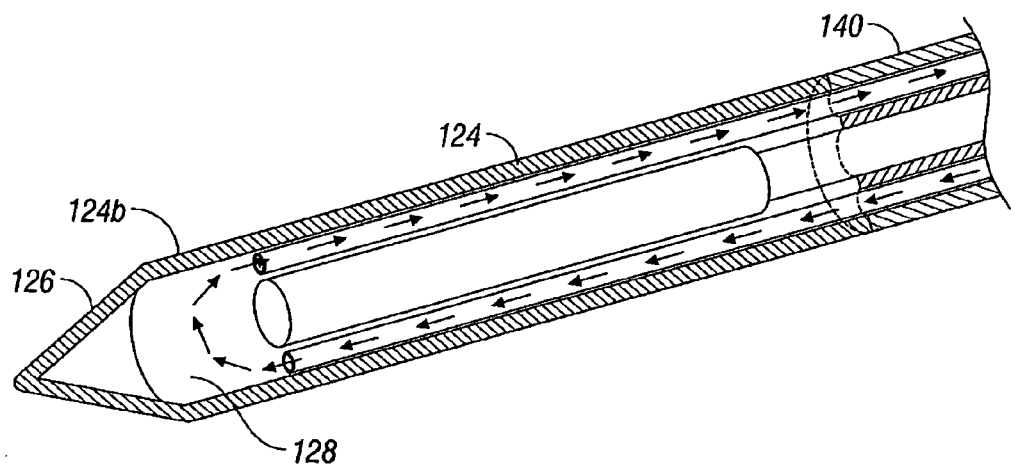

In yet another embodiment, as seen in FIG. 7D, distal end 124b of sheath 124 is closed and formed integrally with penetrating member 126 such that cavity 128 is defined by sheath 124, sealing barrier 140, and penetrating member 126.

Figure 7E:
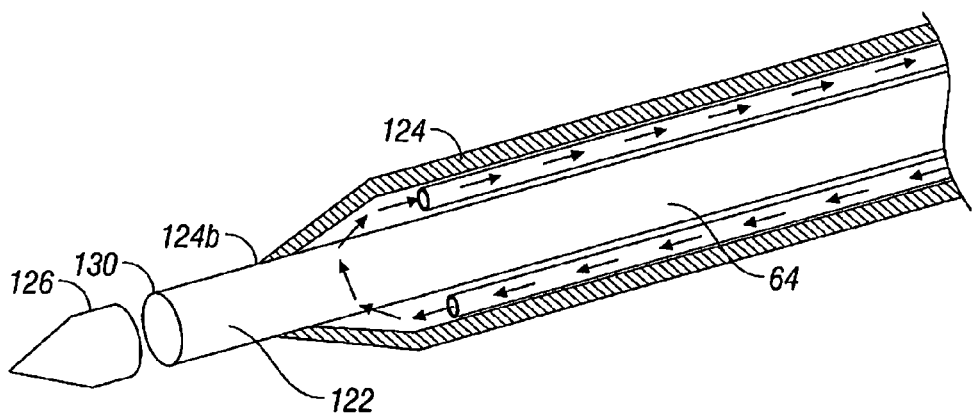

In still another embodiment, as best seen in FIG. 7E, a distal-most tip 130 of radiating section 122 of inner conductor 64 extends beyond distal end 124b of sheath 124. In this embodiment, penetrating member 126 may be connected directly to radiating section 122.

Figure 7F:
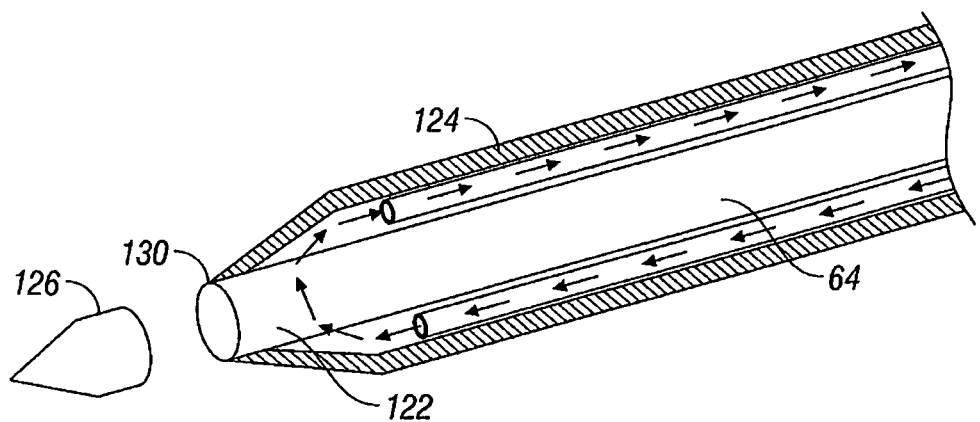

As seen in FIG. 7F, sheath 124 may also be connected directly to radiating section 122 of inner conductor 64 at its distal-most tip 130. In this embodiment, penetrating member 126 is connected either to sheath 124 or to radiating section 122.

With respect to each of the aforementioned embodiments, sheath 124 may be formed of any biocompatible material suitable for the intended purpose of retaining a fluid therein while allowing for the dispersion of microwave energy. It is contemplated that the sheath 124 may be formed, in whole or in part, of a substantially rigid or a substantially non-rigid material. For example, in those embodiments wherein the inner conductor 64b is electrically connected to sheath 124, sheath 124 can be formed from stainless steel. Additionally, the connection between penetrating member 126 may be either releasably or fixedly coupled with antenna assembly 100 in any suitable manner.

Figure 8:
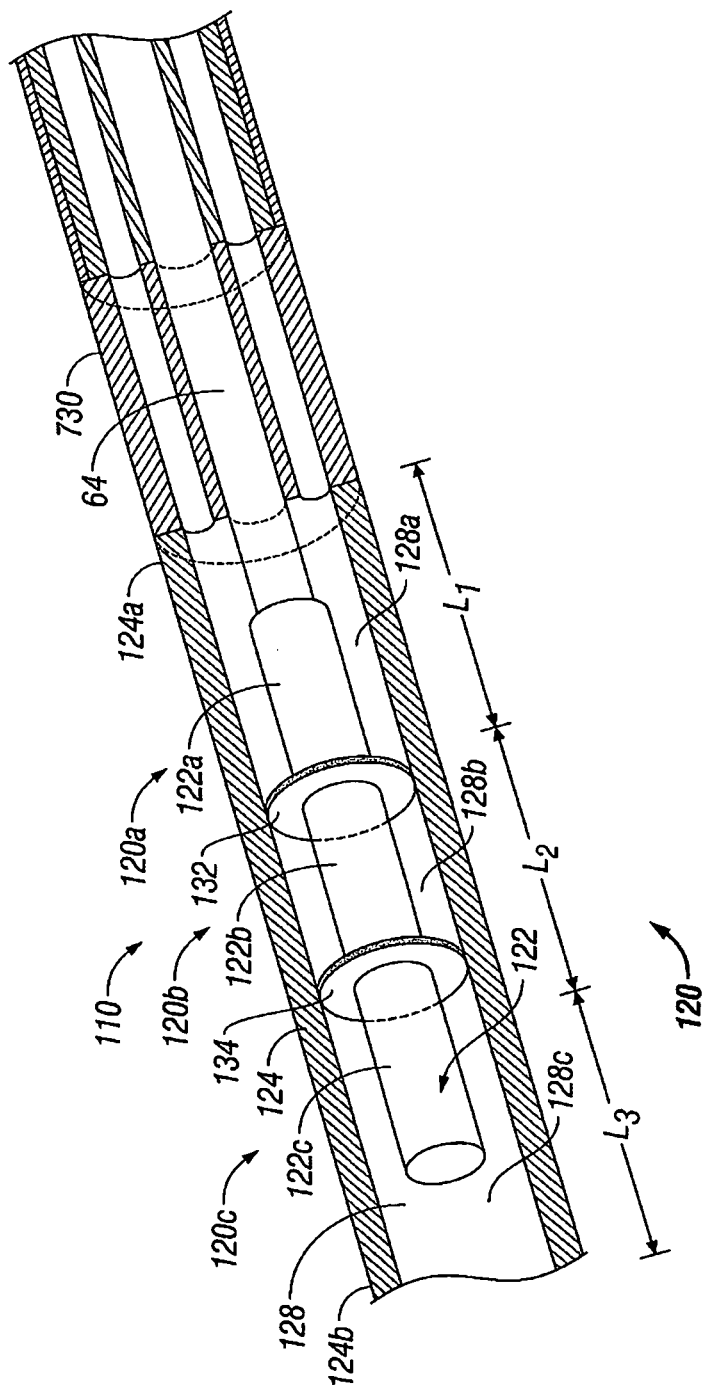
FIG. 8 is a schematic, cross-sectional view of distal and radiating portions of a microwave tissue treatment device, in accordance with an embodiment of the present disclosure.

Referring now to FIG. 8, cavity 128 may include one or more internal baffle members 132, 134 that divide radiating portion 120 into respective proximal, intermediate, and distal regions 120a, 120b, and 120c. Additionally, the baffle members 132, 134 act to divide cavity 128 into respective proximal, intermediate, and distal cells 128a, 128b, 128c, and radiating section 122 into respective first, second, and third segments 122a, 122b, 122c. Although the particular embodiment shown in FIG. 8 includes two baffle members, any suitable number of baffle members may be employed to divide radiating portion 120, cavity 128, and radiating section 122 into any suitable number of regions, cells, and segments, respectively.

Proximal cell 128a of cavity 128, and consequently, first segment 122a of radiating section 122 of inner conductor 64, exhibit a first axial dimension $L_1$, and are defined by first baffle member 132 and the location where proximal end 124a of the sheath 124 meets sealing barrier 140. Intermediate cell 128b of cavity 128, and consequently, second segment 122b of radiating section 122 exhibit a second axial dimension $L_2$, and are defined by the location of first baffle member 132 and second baffle member 134. Distal cell 128c of cavity 128 and third segment 122c of radiating section 122 exhibit a third axial dimension $L_3$, and are defined by the location of second baffle member 134 and distal end 126c of sheath 124.

First and second baffle members 132, 134, respectively, serve not only to partially define the metes of the three cells 128a, 128b, 128c of cavity 128 defined by sheath 124, but also to substantially prevent any co-mingling of fluid or fluids (not shown) that may be circulated throughout each of the respective proximal, intermediate, and distal regions 120a, 120b, 120c of the radiating portion 120, as discussed in further detail herein below.

With continued reference to FIG. 8, distal region 120c of radiating portion 120 of antenna assembly 100 may comprise the area of active heating during tissue treatment or ablation. It may be desirable, therefore, to prevent the temperature in distal region 120c from reaching excessively high temperatures in order to maintain optimal energy delivery and to maintain optimal thermal therapy of the tissue. Intermediate region 120b may also become hot due to ohmic and conductive heating from distal region 120c. Since intermediate region 120b may be in contact with the tissue surrounding the target site, it may be desirable to allow intermediate region 120b to achieve a particular temperature profile dependent upon the nature of the surgical procedure being performed.

As an illustrative example, where coagulation of the insertion tract may be desirable, the clinician may want to allow intermediate region 120b of radiating portion 120 to attain a particular predetermined temperature capable of creating a coagulation effect in the insertion tract. In other applications, it may also be desirable, to prevent the temperature in intermediate region 120b from rising beyond a particular threshold level to protect surrounding sensitive tissue structures from undesired effects.

During use, proximal region 120a of radiating portion 120 may also come into contact with the skin or tissue of a patient. As proximal region 120a may also be subject to ohmic and/or conductive heating, it may be desirable to maintain the temperature of proximal region 120a below a specific temperature, particularly in percutaneous or laparoscopic procedures, to mitigate or substantially prevent any undesired effects upon the patient's tissue. In other procedures, such as in applications where lesions are located deep within the tissue, it may be desirable to allow the proximal region 120a to become heated to allow for the coagulation of the insertion tract.

Referring now to FIG. 1 as well, the specific components and features of the presently disclosed cooling system 180 reduce the radial or transverse dimensions of antenna assembly 100, thereby potentially improving the performance of the antenna assembly 100. However, reducing the dimensions of antenna assembly 100 may necessitate an increase in the amount of energy flowing through antenna assembly 100 to achieve the same therapeutic effect that could otherwise be achieved by using a larger, more conventional antenna assembly and lower energy levels. The presently disclosed cooling system 180 reduces the likelihood that the increased amount of energy flowing through antenna assembly 100 will have negative results, e.g., losses, overheating, and potential failure of microwave tissue treatment device 20, and counteracts the impact of any such results should they occur.

Figure 9:
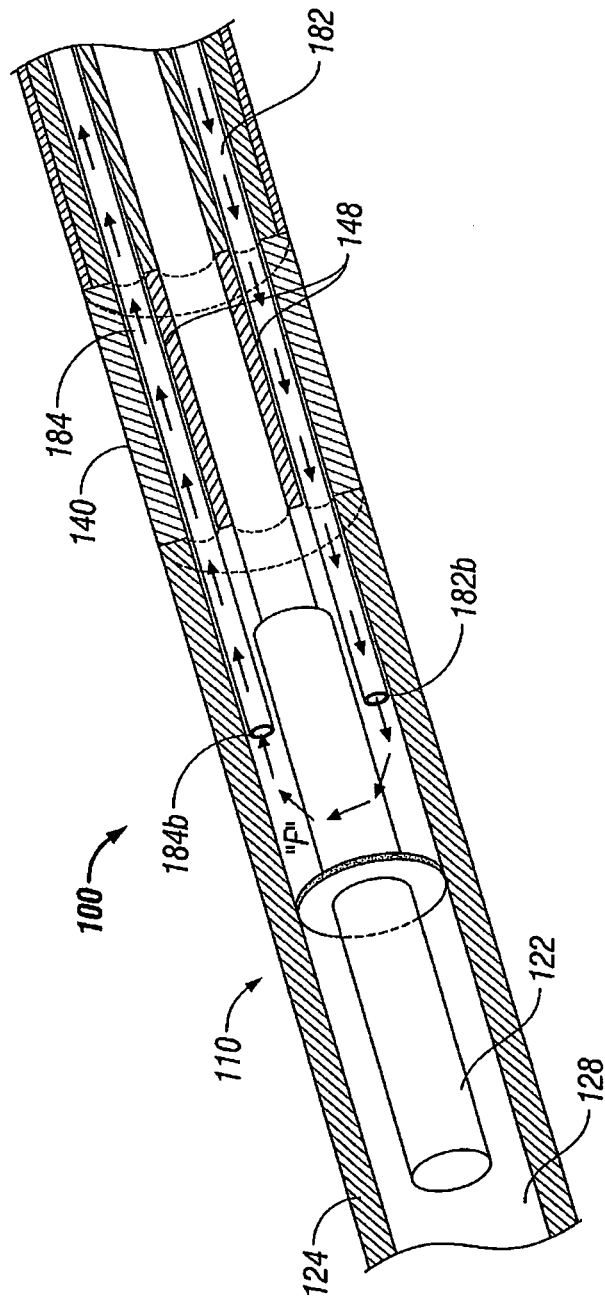
FIG. 9 is a schematic, cross-sectional, perspective view of distal and radiating portions of a microwave tissue treatment device including a cooling system, in accordance with another embodiment of the present disclosure.

Referring now to FIGS. 1 and 9, cooling system 180 will be discussed. Cooling system 180 is adapted to circulate a fluid "F", either constantly or intermittently, throughout radiating portion 120 (FIG. 1) of antenna assembly 100. Fluid "F" may be a liquid, e.g., water, saline, liquid chlorodifluoromethane, perfluorocarbon, such as Fluorinert®, distributed commercially by Minnesota Mining and Manufacturing Company (3M), St. Paul, Minn., USA, or any combination thereof. In various embodiments, gases, such as air, nitrous oxide, nitrogen, carbon dioxide, etc., may be utilized as an alternative to, or in conjunction with, any of the aforementioned liquids. The composition of fluid "F" may be varied depending upon the desired cooling rate and the desired impedance of the feedline 60.

Cooling system 180 includes an inlet conduit 182 having a proximal end 182a (FIG. 1) and a distal end 182b (FIG. 9), and an outlet conduit 184 having a proximal end 184a (FIG. 1) and a distal end 184b (FIG. 9). Proximal ends 182a, 184a of inlet and outlet conduits 182, 184, respectively, are connected to, and are in fluid communication with, pump 80 (FIG. 1), and distal ends 182b, 184b of inlet and outlet conduits 182, 184, respectively, are in fluid communication with cavity 128 (FIG. 9) defined by sheath 124. Inlet and outlet conduits 182, 184, respectively, act in concert with pump 80 to circulate fluid "F" through cavity 128, thereby cooling radiating section 122 of inner conductor 64 (see, e.g., FIG. 2A). Cooling system 180 may include any number of inlet and outlet conduits 182, 184 suitable for the intended purpose of circulating dissipative fluid "F" throughout cavity 128.

With additional reference to FIGS. 3 and 4A-4B, the respective inlet and outlet conduits 182, 184 extend from pump 80 and enter conduits 164a, 164b of connecting hub 160. The respective inlet and outlet conduits 182, 184 pass through elongate member 62 and enter channels 72a-72d formed in distal portion 68b of dielectric 68 through apertures 166 formed in connecting hub 160. The respective inlet and outlet conduits 182, 184 extend distally through channels 148 (FIG. 9) formed in sealing barrier 140 and into radiating portion 120 (FIG. 1) of antenna assembly 100, thereby facilitating the circulation of fluid "F" within the radiating portion 120

Including a cooling system 180, e.g., the respective inlet and outlet conduits 182, 184, that extends through the dielectric 68, as opposed a cooling system that includes an external cooling chamber that is positioned about the antenna assembly 100, creates a size reduction benefit. That is, by eliminating the need for an external cooling chamber, the transverse outer dimension of the outer conductor 66b will constitute the transverse outer dimension of the antenna assembly 100. This allows for the employment of larger inner and outer conductors 64b, 66b, respectively, which reduces loss effects, without increasing the overall transverse dimension of the antenna assembly 100.

Figure 10:
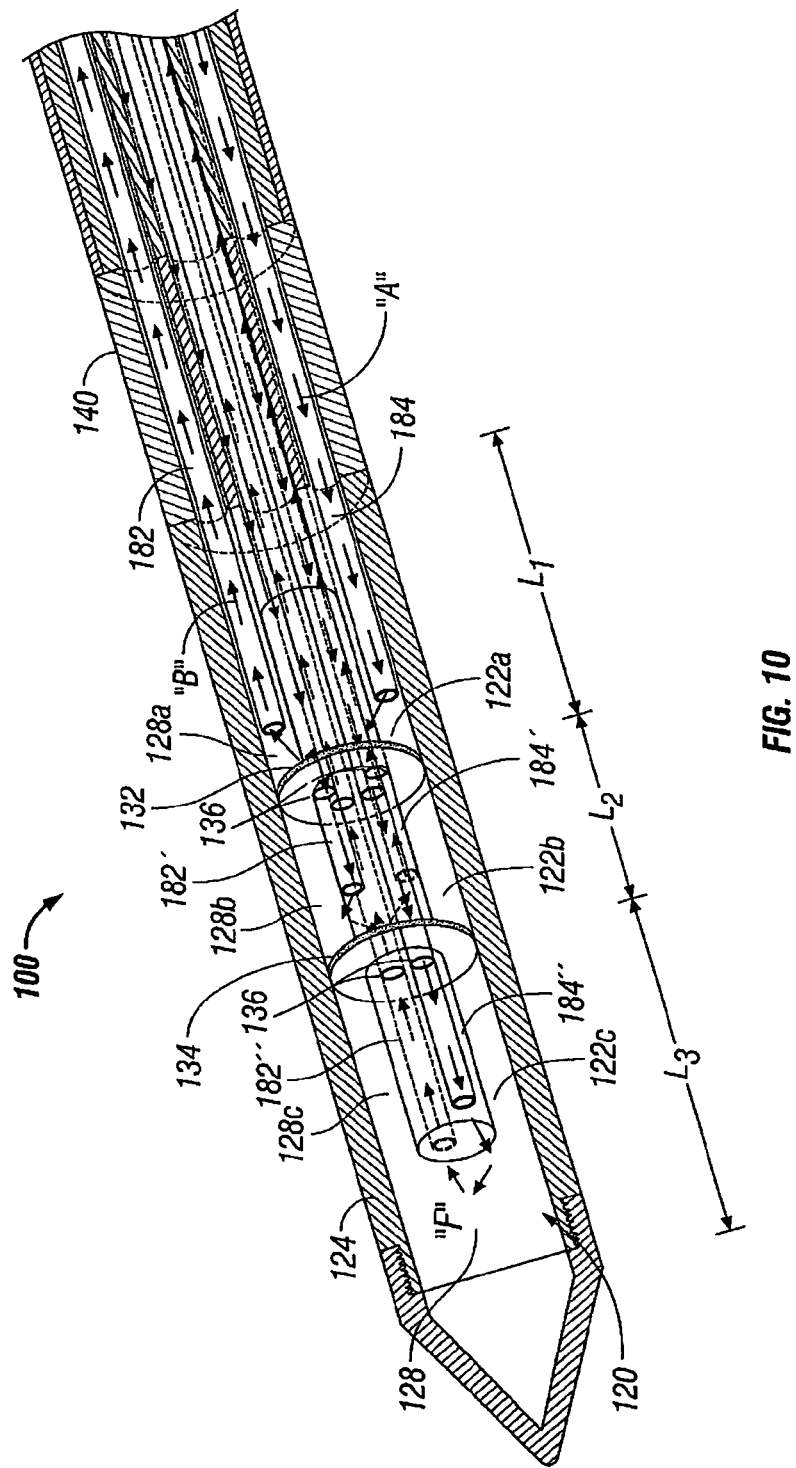
FIG. 10 is a schematic, cross-sectional, perspective view of an embodiment of distal and radiating portions of the microwave tissue treatment device of FIG. 9.

As seen in FIG. 10, in one embodiment, the number of respective inlet and outlet conduits 182, 184 corresponds to the number of regions, segments, and cells of the radiating portion 120 of antenna assembly 100, radiating section 122 of inner conductor 64, and cavity 128, respectively. In particular, inlet and outlet conduits 182', 184' circulate fluid "F" throughout proximal cell 128a of cavity 128 such that fluid "F" may contact proximal segment 122a of radiating section 122, and thereby cool proximal region 120a of radiating portion 120 of assembly 100. In likewise fashion, respective inlet and outlet conduits 182", 184" circulate fluid "F" throughout intermediate cell 128b of cavity 128 such that fluid "F" may contact intermediate segment 122b of radiating section 122, and thereby cool intermediate region 120b of radiating portion 120 of antenna assembly 100, and respective inlet and outlet conduits 182'", 184'" circulate fluid "F" throughout distal cell 128c of cavity 128 such that fluid "F" may contact distal segment 122c of radiating section 122, and thereby cool distal region 120c of radiating portion 120 of antenna assembly 100. While FIG. 10 depicts each cell 128a-128c in contact with fluid "F," the present disclosure also envisions, the alternative, that fluid "F" may not be circulated through one or more of cells 128a-128c.

Referring still to FIG. 10, upon entering proximal cell 128a through inlet conduit 182', i.e., in the direction of arrows "A", fluid "F" comes into direct contact with proximal segment 122a of radiating section 122 of inner conductor 64, allowing for the direct convective cooling thereof. As the fluid "F" cools proximal segment 122a, pump 80 (FIG. 1) removes fluid "F" from proximal cell 128a, in the direction of arrows "B", through outlet conduit 184'. In so doing, the heat generated by proximal segment 122a during the operation of antenna assembly 100 may be regulated and/or dissipated. Accordingly, the temperature of proximal region 120a of radiating portion 120 may be controlled.

As with proximal cell 128a, fluid "F" may be circulated into and out of intermediate cell 128b by pump 80 (FIG. 1) through inlet and outlet conduits 182", 184", respectively, thereby dissipating the heat generated by the intermediate segment 122b during the operation of antenna assembly 100 through fluid "F".

Similarly, fluid "F" may be circulated into and out of the distal cell 128c by pump 80 (FIG. 1) through inlet and outlet conduits 182'", 184'", respectively, thereby dissipating the heat generated by the distal segment 122c during the operation of antenna assembly 100 through fluid "F".

To circulate fluid "F" through proximal cell 128a of cavity 128, inlet and outlet conduits 182', 184' pass through corresponding channels 148 (FIGS. 6, 9) in sealing barrier 140. To circulate fluid "F" through intermediate cell 128b, inlet and outlet conduits 182", 184" pass through channels 148, as well as through apertures 136 in first baffle member 132. To circulate fluid "F" through distal cell 128c, inlet and outlet conduits 182'", 184'" pass through channels 148, through apertures 136 in first baffle member 132, through intermediate cell 128b, and finally through apertures 136 in second baffle member 134.

Sealing barrier 140, first baffle member 132, and second baffle member 134 may each include seal members (not shown) respectively associated with channels 148 and apertures 136 to substantially prevent fluid "F" from commingling between cells 128a-128c of cavity 128, and the seal members may be any member suitable for this intended purpose including but not being limited to seals, gaskets, or the like. The seal members may be formed of any suitable material, including but not being limited to, a polymeric material.

Referring still to FIG. 10, given the desirability of controlling heating and temperature regulation within the individual segments 122a-122c of radiating section 122 (FIG. 9) of inner conductor 64 (see, e.g., FIG. 2A), and the corresponding regions 120a-120c of radiating portion 120 of antenna assembly 100, the axial locations of baffle members 132, 134 within cavity 128 may be varied as desired or necessary such that the respective axial dimensions $L_1$, $L_2$, and $L_3$ of the proximal, intermediate, and distal cells 128a-128c of cavity 128 may also be varied. In varying the axial length of a particular cell of cavity 128, the overall volume of that cell may be varied, and consequently, so too may the volume of fluid "F" circulated therein. As would be appreciated by one of ordinary skill in the art, an inverse relationship exists between the volume of fluid "F" within a particular cell of cavity 128 and the temperature of the corresponding region of radiating portion 120, in that as the volume of fluid "F" is increased, the temperature of the region will decrease.

Baffle members 132, 134 may be located at any suitable or desired point within the cavity 128. In one embodiment, baffle members 132, 134 may be positioned such that the respective first, second and third axial dimensions, $L_1$, $L_2$, and $L_3$ of proximal, intermediate, and distal cells 128a-128c are substantially equivalent. In another embodiment, baffle members 132, 134 are positioned such that the first axial dimension $L_1$ of proximal cell 128a is greater than the respective second and third axial dimensions $L_2$ and $L_3$ of intermediate and distal cells 128b, 128c. In yet another embodiment, baffle members 132, 134 may be positioned such that the third axial dimension $L_3$ of distal cell 128c is greater than the respective first and second axial dimensions $L_1$ and $L_2$ of proximal and intermediate cells 128a, 128b. In alternative embodiments, baffle members 132, 134 may be located such that the overall volume of the cavity 128 may be distributed amongst any individual cells thereof in any suitable manner.

Figure 11:
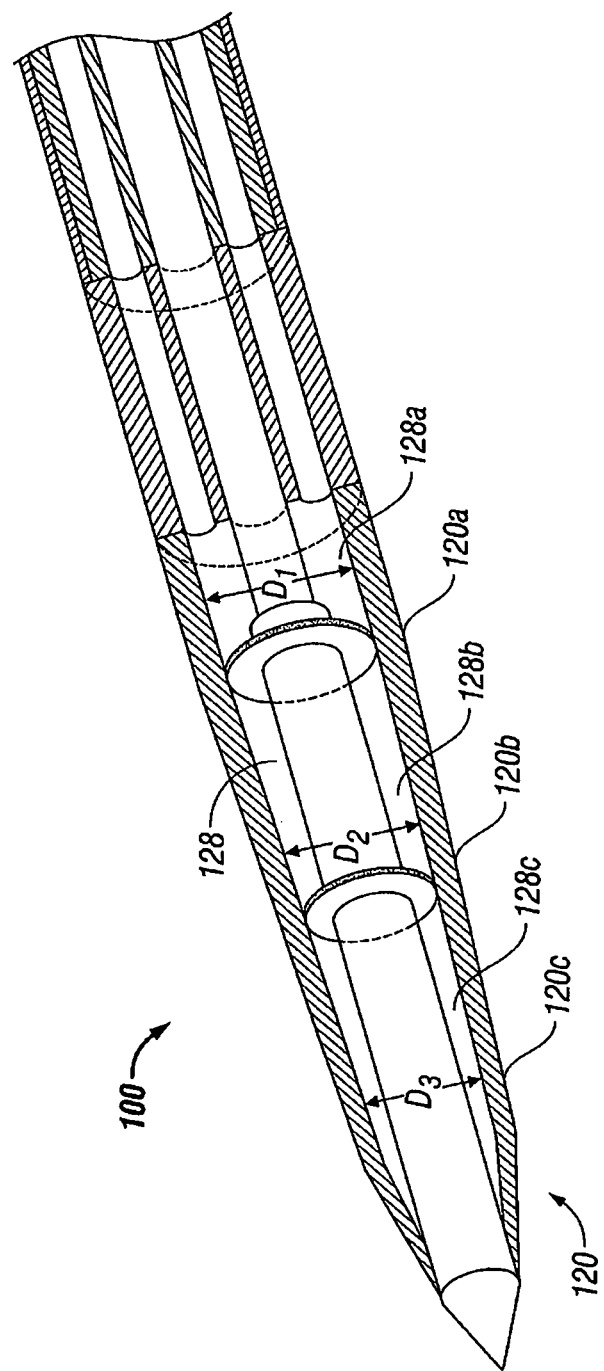
FIG. 11 is a schematic, cross-sectional, perspective view of distal and radiating portions of an antenna assembly of a microwave tissue treatment device in accordance with another embodiment of the present disclosure.

With reference now to FIG. 11, in another embodiment, proximal, intermediate, and distal cells 128a, 128b, 128c of cavity 128 define respective first, second, and third radial dimensions $D_1$, $D_2$, and $D_3$. As shown, radial dimension $D_1$ is greater than radial dimension $D_2$, which is in turn greater than radial dimension $D_3$. However, the respective first, second, and third radial dimensions $D_1$, $D_2$, and $D_3$ may also be substantially equivalent.

The respective radial dimensions $D_1$, $D_2$, and $D_3$ of proximal, intermediate, and distal cells 128a, 128b, 128c may be varied in any suitable manner so as to regulate the volume thereof, and consequently, the volume of fluid "F" that may be circulated therethrough. By varying the volume of fluid "F" circulated through each cell 128a-128c of cavity 128, the temperature of each corresponding region 120a-120c of radiating portion 120 of antenna assembly 100 may be substantially regulated, as discussed above.

Figure 12:
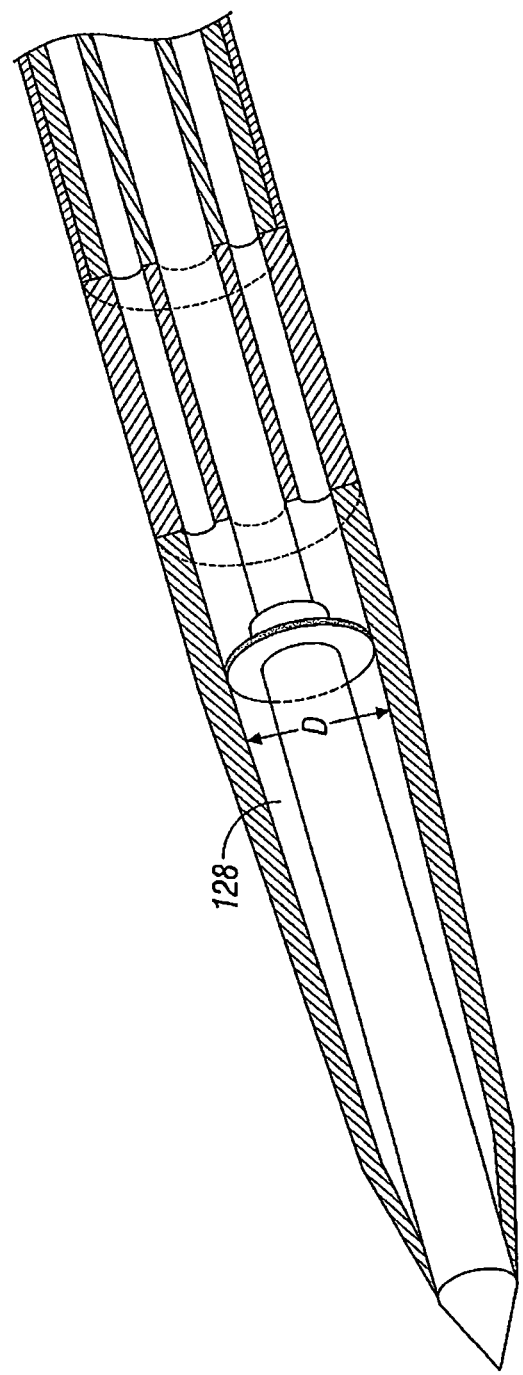
FIG. 12 is a schematic, cross-sectional, perspective view of distal and radiating portions of an antenna assembly of a microwave tissue treatment device in accordance with yet another embodiment of the present disclosure.

As seen in FIG. 12, in another embodiment, cavity 128 defines a radial dimension D that is varied in a continuously decreasing manner over the axial length thereof such that a generally tapered profile is exhibited. The tapered profile exhibited in this embodiment may also be applied to any of the embodiments disclosed herein above.

Figure 13:
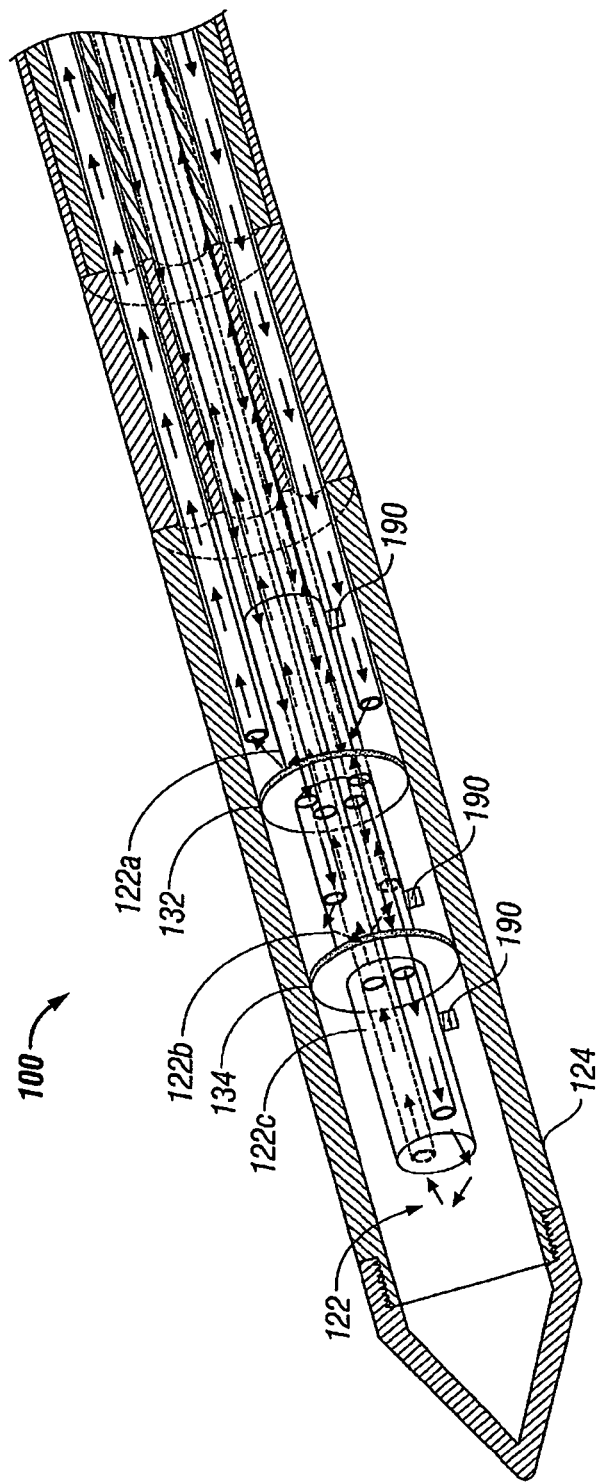
FIG. 13 is a schematic, cross-sectional, perspective view of distal and radiating portions of an antenna assembly of a microwave tissue treatment device in accordance with still another embodiment of the present disclosure.

FIG. 13 illustrates yet another embodiment in which antenna assembly 100 includes one or more temperature sensors 190 adapted, coupled, or operatively connected to segments 122a-122c of radiating section 122 of inner conductor 64. Temperature sensors 190 may be used to monitor any fluctuation in temperature in regions 120a-120c of radiating portion 120. It may be desirable to monitor the temperature of the radiating portion 120, and/or the tissue that may come into contact therewith, in an effort to guard against over heating and/or any unintended therapeutic effects on the tissue. This may be particularly useful in applications where microwave energy is used for treating or ablating tissue around the radiating portion. In alternative embodiments, temperature sensors 190 may be adapted, coupled, operatively connected, or incorporated into antenna assembly 100 at any suitable location, including, but not being limited to on sheath 124. Temperature sensors 190 may be located on or within the sheath 124 using any conventional means, e.g., adhesives. Temperature sensors 190 may also be located on one or more baffle members, e.g., baffle member 132, 134, if any. Temperature sensors 190 may be configured and adapted for electrical connection to a power supply 40 (FIG. 1).

Temperature sensors 190 may be a semiconductor-based sensor, a thermistor, a thermal couple or other temperature sensor that would be considered as suitable by one skilled in the art. An independent temperature monitor (not shown) may be connected to the temperature sensor, or alternatively, power supply 40 (FIG. 1) may include an integrated temperature monitoring circuit (not shown), such as one described in U.S. Pat. No. 5,954,719, to modulate the microwave power output supplied to antenna assembly 100. Other physiological signals, e.g. EKG, may also be monitored by additional medical instrumentation well known to one skilled in the art and such data applied to control the microwave energy delivered to the antenna assembly 100.

A closed loop control mechanism, such as a feedback controller with a microprocessor, may be implemented for controlling the delivery of energy, e.g., microwave energy, to the target tissue based on temperature measured by temperature sensors 190.

The above description, disclosure, and figures should not be construed as limiting, but merely as exemplary of particular embodiments. It is to be understood, therefore, that the disclosure is not limited to the precise embodiments described, and that various other changes and modifications may be effected therein by one skilled in the art without departing from the scope or spirit of the disclosure. Additionally, persons skilled in the art will appreciate that the features illustrated or described in connection with one embodiment may be combined with those of another, and that such modifications and variations are also intended to be included within the scope of the present disclosure.

What is claimed is:

1. A microwave tissue treatment device, comprising:
   an antenna assembly having proximal and distal ends, the antenna assembly including:
      an elongate member;
      an outer conductor positioned within the elongate member;
      a dielectric material disposed within the outer conductor, at least a portion of the dielectric material defining a lumen and at least one longitudinally extending channel;
      an inner conductor having a distal radiating section, at least a portion of the inner conductor being at least partially disposed within the lumen of the dielectric material;
      a first baffle member disposed adjacent a distal end of the outer conductor forming a first cooling chamber;
      a second baffle member disposed proximally of the first baffle member forming a second cooling chamber;
      a radiating-portion disposed adjacent the first baffle member, the radiating-portion including the distal radiating section of the inner conductor and a sheath at least partially disposed about and spaced from the distal radiating section of the inner conductor; and
   a cooling system including:
      a first inlet conduit and a first outlet conduit, wherein the first inlet conduit and the first outlet conduit are disposed within a distal segment of the distal radiating section and are configured to circulate a fluid within the first cooling chamber;
      a second inlet conduit and a second outlet conduit, wherein the second inlet conduit and the second outlet conduit are configured to circulate a fluid within the second cooling chamber, the dielectric material separating the at least one longitudinally extending channel from the lumen to insulate the first and second inlet and outlet conduits from the inner conductor;
      a first temperature sensor operably associated with the first cooling chamber; and
      a second temperature sensor operably associated with the second cooling chamber.

2. The microwave tissue treatment device of claim 1, further including a penetrating member supported at the distal end of the antenna assembly.

3. The microwave tissue treatment device of claim 1, wherein the at least one longitudinally extending channel of the dielectric material includes at least a first channel and a second channel.

4. The microwave tissue treatment device of claim 3, wherein the first inlet conduit of the cooling system is at least partially disposed in the first channel and the first outlet conduit of the cooling system is at least partially disposed in the second channel.

5. The microwave tissue treatment device of claim 1, wherein the antenna assembly further includes a connecting hub at least partially disposed about the elongate member, the connecting hub being located proximally of the first baffle member.

6. The microwave tissue treatment device of claim 1, wherein the cooling system is configured to circulate a heat dissipative fluid.

7. The microwave tissue treatment device of claim 1, wherein the cooling system is configured to circulate a heat dissipative fluid selected from the group consisting of water, saline, ammonium chloride, sodium nitrate, and potassium chloride.

8. The microwave tissue treatment device of claim 5, wherein the connecting hub includes a first conduit configured and dimensioned to receive the second inlet conduit and a second conduit configured and dimensioned to receive the second outlet conduit of the cooling system.

9. The microwave tissue treatment device of claim 1, wherein the outer conductor includes at least a first aperture configured and dimensioned to receive the second inlet conduit and at least a second aperture configured and dimensioned to receive the second outlet conduit.

10. An improved microwave tissue treatment device having an antenna assembly that includes an outer conductor, an inner conductor having a radiating section, and a radiating-portion that includes the radiating section of the inner conductor and a sheath at least partially disposed thereabout such that a distal cooling chamber in fluid communication with the radiating section is defined and a proximal cooling chamber is defined, the microwave tissue treatment device comprising:
   a cooling system including a first inlet conduit, a second inlet conduit, a first outlet conduit, and a second outlet conduit, the first inlet conduit and the first outlet conduit disposed within a distal segment of the radiating section and in fluid communication with the distal cooling chamber, and the second inlet conduit and the second outlet conduit being in fluid communication with the proximal cooling chamber;
   a dielectric material disposed within the outer conductor, the dielectric material defining a lumen, a first channel, and a second channel extending longitudinally therethrough, the lumen being configured and dimensioned to at least partially receive at least a portion of the inner conductor, the first longitudinally extending channel being configured and dimensioned to at least partially receive the first inlet conduit, and the second longitudinally extending channel being configured and dimensioned to at least partially receive the first outlet conduit of the cooling system, the dielectric material separating the first and second channels from the lumen to insulate the first and second inlet and outlet conduits from the inner conductor;
   a distal temperature sensor operatively associated with the distal cooling chamber; and
   a proximal temperature sensor operatively associated with the proximal cooling chamber.

11. The improved microwave tissue treatment device of claim 10, further including at least one baffle member disposed between the inner conductor and the sheath, the at least one baffle member at least partially defining the proximal and distal cooling chambers.

12. A method of cooling a microwave antenna which includes an inner conductor having a distal radiating section, an outer conductor, a distal cooling chamber, a proximal cooling chamber, and a dielectric material, the method comprising:
   providing a cooling system including:
      a first inlet conduit and a first outlet conduit disposed at least partially within corresponding channels formed in the dielectric material, the first inlet conduit and the first outlet conduit disposed within a distal segment of the radiating section and in fluid communication with the distal cooling chamber; and
      a second inlet conduit and a second outlet conduit disposed at least partially within the dielectric material, the second inlet conduit and the second outlet conduit being in fluid communication with the proximal cooling chamber, the dielectric material separating and insulating the first and second inlet and outlet conduits from the inner conductor;
   circulating a first cooling fluid through the first inlet conduit and the first outlet conduit of the cooling system such that the first cooling fluid is in fluid communication with the distal cooling chamber and at least a portion of the inner conductor;
   circulating a second cooling fluid through the second inlet conduit and the second outlet conduit of the cooling system such that the second cooling fluid is in fluid communication with the proximal cooling chamber;
   sensing a temperature of the distal cooling chamber; and
   sensing a temperature of the proximal cooling chamber.

13. The method of claim 12, further including regulating circulation of the first and second cooling fluids with a pump in communication with the cooling system.

14. The method of claim 12, further including regulating microwave energy delivery in accordance with a sensed temperature of the distal cooling chamber.

15. The method of claim 12, further including regulating microwave energy delivery in accordance with a sensed temperature of the proximal cooling chamber.

16. The microwave tissue treatment device of claim 3, wherein the second inlet conduit of the cooling system is at least partially disposed in the first channel and the second outlet conduit of the cooling system is at least partially disposed in the second channel.

* * * * *